(12) United States Patent
Madhusudhana et al.

(10) Patent No.: US 11,048,317 B2
(45) Date of Patent: Jun. 29, 2021

(54) GAS SENSOR AUGMENTED HUMAN PRESENCE DETECTION SYSTEM

(71) Applicant: MOTOROLA MOBILITY LLC, Chicago, IL (US)

(72) Inventors: Nikhil Ambha Madhusudhana, Chicago, IL (US); Vivek K. Tyagi, Chicago, IL (US); Joseph V. Nasti, Chicago, IL (US); Scott Debates, Frisco, TX (US)

(73) Assignee: Motorola Mobility LLC, Chicago, IL (US)

( * ) Notice: Subject to any disclaimer, the term of this patent is extended or adjusted under 35 U.S.C. 154(b) by 184 days.

(21) Appl. No.: 16/289,613

(22) Filed: Feb. 28, 2019

(65) Prior Publication Data

US 2020/0278741 A1    Sep. 3, 2020

(51) Int. Cl.
*G06F 3/048* (2013.01)
*G06F 21/60* (2013.01)
*H04W 52/02* (2009.01)
*G06F 1/3231* (2019.01)
(Continued)

(52) U.S. Cl.
CPC .......... *G06F 1/3231* (2013.01); *G01C 21/12* (2013.01); *G01N 33/004* (2013.01); *G01S 19/42* (2013.01);
(Continued)

(58) Field of Classification Search
CPC .......... G06F 3/01; G06F 21/00; G06F 1/3231; G06F 3/048; G06F 21/60; G06F 3/011; G06F 3/167; G06F 21/6245; H04W 52/02; H04W 48/04; H04W 4/029; G01C 21/12; G01N 33/004; G01S 19/42; G06K 9/00664; G10L 25/51; H04R 29/00
See application file for complete search history.

(56) References Cited

U.S. PATENT DOCUMENTS

2006/0179853 A1\* 8/2006 Vosburgh ............. B60H 3/0085
62/126
2014/0157424 A1\* 6/2014 Lee ...................... G06F 21/6245
726/26
(Continued)

OTHER PUBLICATIONS

Mao, Xufei et al., "CitySee: Urban CO2 Monitoring with Sensors", International Conference on Computer Communications, 2012.

*Primary Examiner* — Hugo Molina
(74) *Attorney, Agent, or Firm* — Isidore PLLC (57) ABSTRACT

A communication device, method, and computer program product provide higher confidence in person detection by augmenting sensing with carbon dioxide sensing and contextual information. The communication device determines a current carbon dioxide level in a space in which the communication device is located. A processor of the communication device compares the current carbon dioxide level to a carbon dioxide baseline threshold that is indicative of presence of a person in the space. In response to determining that the current carbon dioxide level is greater than the carbon dioxide baseline threshold, the processor further determines whether at least one target is sensed within the space. In response to determining that at least one target is sensed in the space, the processor infers the presence of a person in the space and sets a control mode of the communication device that correlates to the presence of the person.

20 Claims, 8 Drawing Sheets

(51) Int. Cl.

| | | |
|---|---|---|
| *G06F 3/01* | (2006.01) | |
| *G01N 33/00* | (2006.01) | |
| *G01C 21/12* | (2006.01) | |
| *G01S 19/42* | (2010.01) | |
| *G06K 9/00* | (2006.01) | |
| *G10L 25/51* | (2013.01) | |
| *H04R 29/00* | (2006.01) | |
| *G06F 21/62* | (2013.01) | |
| *G06F 3/16* | (2006.01) | |
| *H04W 4/029* | (2018.01) | |
| *H04W 48/04* | (2009.01) | |

(52) U.S. Cl.
CPC .............. *G06F 3/011* (2013.01); *G06F 3/048* (2013.01); *G06F 3/167* (2013.01); *G06F 21/60* (2013.01); *G06F 21/6245* (2013.01); *G06K 9/00664* (2013.01); *G10L 25/51* (2013.01); *H04R 29/00* (2013.01); *H04W 4/029* (2018.02); *H04W 48/04* (2013.01)

(56) References Cited

U.S. PATENT DOCUMENTS

| | | | | |
|---|---|---|---|---|
| 2015/0319553 | A1* | 11/2015 | Grumbles, III | H04Q 9/00 |
| | | | | 702/188 |
| 2016/0335488 | A1* | 11/2016 | Nongpiur | G10L 25/18 |
| 2017/0329399 | A1* | 11/2017 | Azam | G06F 1/3265 |
| 2018/0087791 | A1* | 3/2018 | Monkkonen | F24F 13/08 |
| 2018/0137264 | A1* | 5/2018 | Kurian | H04W 4/44 |
| 2020/0053651 | A1* | 2/2020 | Lee | G06F 1/3231 |

\* cited by examiner

GAS SENSOR AUGMENTED HUMAN PRESENCE DETECTION SYSTEM

BACKGROUND

1. Technical Field

The present disclosure relates generally to communication devices and in particular to communication devices configured with sensors to detect a presence of a human person.

2. Description of the Related Art

Communication devices such as smart phones are increasingly used in hands free operations to provide various services such as communication and navigation. For example, in hands free mode, the communication device enables the user to drive more safely, without having to view or directly manipulate controls of the communication device. Features such as always-on voice controls further facilitate user interaction with the communication device.

As another feature, many communication devices use various target sensing capabilities of the communication device to infer whether a person is in proximity. Target sensing by the communication device can be insufficient to confidently infer, and respond to, the presence of a person. For example, a person other than a user can be out of the field of view of a sensor such as a camera of the communication device. The person can be close enough to eavesdrop on audio or visual outputs, compromising personal privacy. For an additional example, the communication device can fail to cutback transmit power as required when a person is close to the communication device.

Target sensing by the communication device can be insufficient to confidently infer, and to respond to, the absence of a person. For example, a microphone of the communication device can inadvertently recognize vocal commands as belonging to the device user that are part of an audio playback on an entertainment system. The communication device can then perform an unauthorized function even with no person present. For a further example, the communication device can incorrectly maintain a user interface in an active state due to inadvertently sensing a user presence based only on audio output, unnecessarily consuming battery power.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

According to aspects of the present innovation, a communication device, method, and a computer program product provide higher confidence in person presence detection by augmenting sensing with carbon dioxide sensing and contextual information. The communication device determines a current carbon dioxide level in a space in which the communication device is located. A processor of the communication device compares the current carbon dioxide level to a carbon dioxide baseline threshold that is indicative of presence of a person in the space. In response to determining that the current carbon dioxide level is greater than the carbon dioxide baseline threshold, the processor further determines whether physical presence of at least one target is sensed within the space. In response to determining the physical presence of at least one target in the space, the processor infers the presence of a person in the space and sets a control mode of the communication device that correlates to the presence of the person. Gas emission sensing augments sensing of physical presence of targets in the space. The correlation of the two disparate types of sensing provides a higher confidence in accurate human presence detection, reducing both false positive and false negative determinations.

In the following detailed description of exemplary embodiments of the disclosure, specific exemplary embodiments in which the various aspects of the disclosure may be practiced are described in sufficient detail to enable those skilled in the art to practice the invention, and it is to be understood that other embodiments may be utilized and that logical, architectural, programmatic, mechanical, electrical and other changes may be made without departing from the spirit or scope of the present disclosure. The following detailed description is, therefore, not to be taken in a limiting sense, and the scope of the present disclosure is defined by the appended claims and equivalents thereof. Within the descriptions of the different views of the figures, similar elements are provided similar names and reference numerals as those of the previous figure(s). The specific numerals assigned to the elements are provided solely to aid in the description and are not meant to imply any limitations (structural or functional or otherwise) on the described embodiment. It will be appreciated that for simplicity and clarity of illustration, elements illustrated in the figures have not necessarily been drawn to scale. For example, the dimensions of some of the elements are exaggerated relative to other elements.

It is understood that the use of specific component, device and/or parameter names, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

As further described below, implementation of the functional features of the disclosure described herein is provided within processing devices and/or structures and can involve use of a combination of hardware, firmware, as well as several software-level constructs (e.g., program code and/or program instructions and/or pseudo-code) that execute to provide a specific utility for the device or a specific functional logic. The presented figures illustrate both hardware components and software and/or logic components.

Those of ordinary skill in the art will appreciate that the hardware components and basic configurations depicted in the figures may vary. The illustrative components are not intended to be exhaustive, but rather are representative to highlight essential components that are utilized to implement aspects of the described embodiments. For example, other devices/components may be used in addition to or in place of the hardware and/or firmware depicted. The depicted example is not meant to imply architectural or other limitations with respect to the presently described embodiments and/or the general invention.

The description of the illustrative embodiments can be read in conjunction with the accompanying figures. Embodiments incorporating teachings of the present disclosure are shown and described with respect to the figures presented herein.

Figure 1:
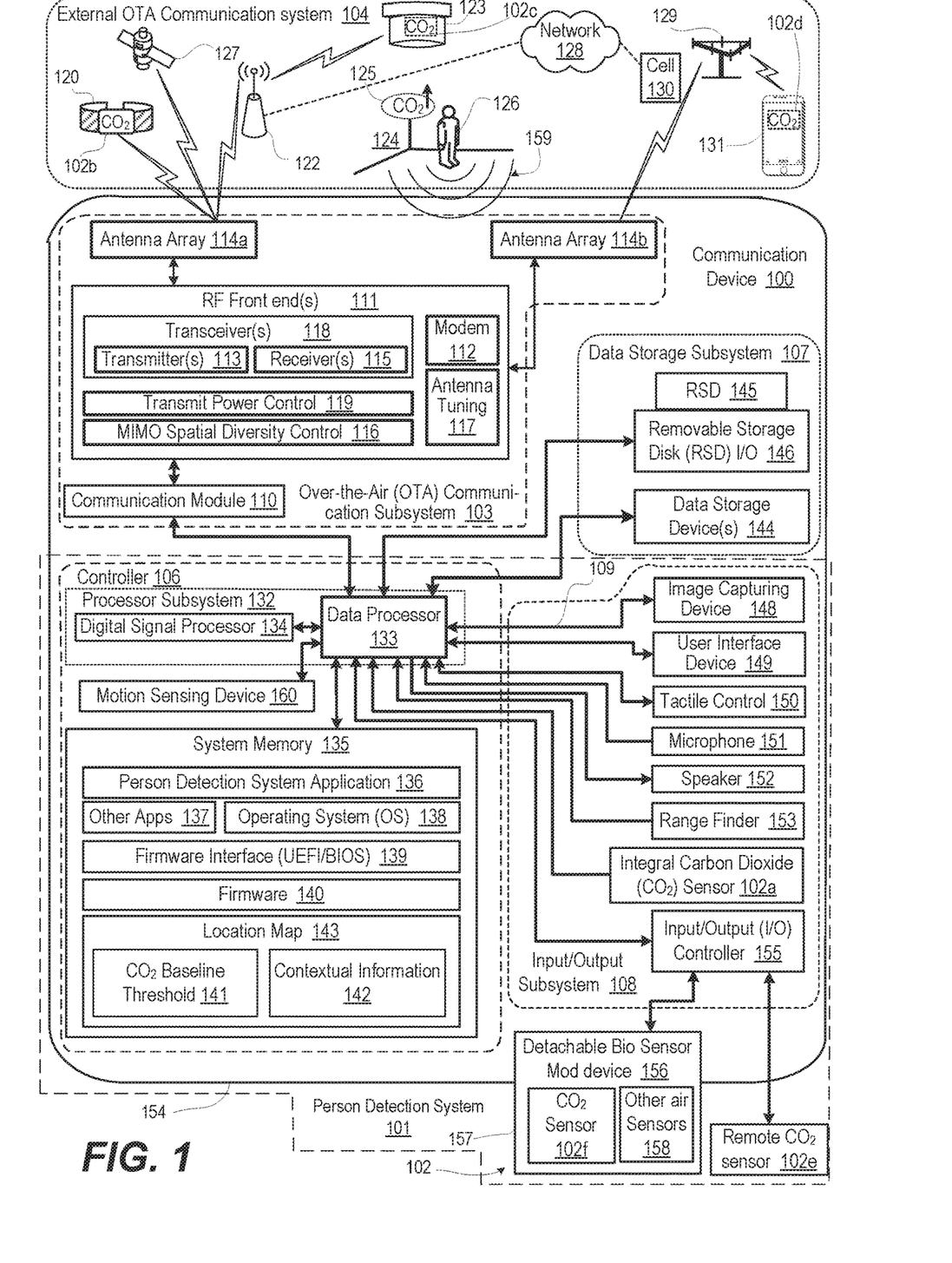
FIG. 1 is a simplified functional block diagram illustrating a communication device that uses a gas sensor augmented human detection system, according to one or more embodiments.

FIG. 1 illustrates example communication device 100 that augments and correlates person detection system 101 with one or more carbon dioxide ($CO_2$) sensors. As used herein, reference numeral "102" refers generally to $CO_2$ sensors that can be integral, attachable, peripheral, or networked to communication device 100. Specific examples of $CO_2$ sensor 102, such as integral $CO_2$ sensor 102a, are introduced below with an alphabetical suffix. Communication device 100 can be one of a host of different types of devices, including but not limited to, a mobile cellular phone or smart-phone, a laptop, a net-book, an ultra-book, a networked smart watch or networked sports/exercise watch, and/or a tablet computing device or similar device that can include wireless communication functionality. As a device supporting wireless communication, communication device 100 can be one of, and also be referred to as, a system, device, subscriber unit, subscriber station, mobile station (MS), mobile, mobile device, remote station, remote terminal, user terminal, terminal, user agent, user device, cellular telephone, a satellite phone, a cordless telephone, a Session Initiation Protocol (SIP) phone, a wireless local loop (WLL) station, a personal digital assistant (PDA), a handheld device having wireless connection capability, a computing device, or other processing devices connected to a wireless modem. These various devices all provide and/or include the necessary hardware and software to support the various wireless or wired communication functions as part of a communication system. Communication device 100 can also be an over-the-air link in a communication system. Communication device 100 can be intended to be portable, hand-held, or fixed in location. Examples of such over-the-air link communication devices 100 include a wireless modem, an access point, a repeater, a wirelessly-enabled kiosk or appliance, a femtocell, a small coverage area node, and a wireless sensor, etc.

Referring now to the specific component makeup and the associated functionality of the presented components, communication device 100 includes over-the-air (OTA) communication subsystem 103 that communicates with external OTA communication system 104. Communication device 100 provides computing and data storage functionality in support of OTA communication with external OTA communication system 104, as well as other functions, with controller 106, data storage subsystem 107, and input/output (I/O) subsystem 108 that are communicatively coupled to each other via a system interlink 109.

OTA communication subsystem 103 includes communication module 110 that operates in baseband to encode data for transmission and decodes received data, according to an applicable communication protocol. OTA communication subsystem 103 includes radio frequency (RF) front end(s) 111 having one or more modems 112. Modems 112 modulate baseband encoded data from communication module 110 onto a carrier signal to provide a transmit signal that is amplified by transmitter(s) 113. Antenna arrays 114a, 114b transmit and receive signals. In one or more embodiments, communication device 100 can include one antenna array 114a. In one or more embodiments, communication device 100 can include more than three antenna arrays (not shown). Modem 112 demodulates the received signal from antenna arrays 114a, 114b. The received signal is amplified and filtered by receiver(s) 115, separating received encoded data from a received carrier signal. Multiple-input multiple-output (MIMO) spatial diversity control 116 can utilize antenna elements within one or more antenna arrays 114a, 114b to actively directionally steer antenna gain to improve communication performance. Antenna tuning circuitry 117 adjusts antenna impedance of antenna arrays 114a, 114b to improve antenna efficiency at desired transmit or receive frequencies of transmitters 113 and receivers 115, respectively, within transceiver(s) 118. RF front end(s) 111 includes transmit power control 119 to adjust uplink transmit power, as required, to effectively communicate with external OTA communication system 104 and to remain within regulated limits.

Controller 106 controls the communication, user interface, and other functions and/or operations of communication device 100. These functions and/or operations include, but are not limited to including, application data processing and signal processing. Communication device 100 may use hardware component equivalents for application data processing and signal processing. For example, communication device 100 may use special purpose hardware, dedicated processors, general purpose computers, microprocessor-based computers, micro-controllers, optical computers, analog computers, dedicated processors and/or dedicated hard wired logic. As utilized herein, the term "communicatively coupled" means that information signals are transmissible through various interconnections, including wired and/or wireless links, between the components. The interconnections between the components can be direct interconnections that include conductive transmission media or may be indirect interconnections that include one or more intermediate electrical components. Although certain direct interconnections (interlink 109) are illustrated in FIG. 1, it is to be understood that more, fewer, or different interconnections may be present in other embodiments.

In one or more embodiments, controller 106, via OTA communication subsystem 103, can perform multiple types of OTA communications with external OTA communication system 104. OTA communication subsystem 103 can communicate with one or more personal access network (PAN) devices, such as smart watch 120 that can include $CO_2$ sensor 102b and that is reached via Bluetooth connection. OTA communication subsystem 103 can communicate with one or more locally networked devices via a wireless local area network (WLAN) link provided by WLAN node 122. For example, a networked fire detector 123 in enclosed space 124 can include $CO_2$ sensor 102c that detects $CO_2$ 125 exhaled by person 126. OTA communication subsystem 103 can communicate with global positioning system (GPS) satellites 127 to obtain geospatial location information. WLAN node 122 is in turn connected to wide area network 128, such as the Internet. OTA communication subsystem 103 can also communicate with radio access network (RAN) 129 having respective base stations (BSs) or cells 130. RANs 129 are a part of a wireless wide area network (WWAN) that is connected to wide area network 128 and provides data and voice services. Other communication devices 131 communicatively coupled to wide area network 128 can include $CO_2$ sensor 102d.

Controller 106 includes processor subsystem 132 that executes program code to provide functionality of the communication device 100. Processor subsystem 132 includes one or more central processing units (CPUs) ("data processor") 133. Processing subsystem 132 can include a digital signal processor (DSP) 134. Controller 106 includes system memory 135 for containing actively used program code and data. System memory 135 can include therein a plurality of such program code and modules, including applications such as human detection system application 136 and other applications 137. System memory 135 can also include operating system (OS) 138, firmware interface 139 such as basic input/output system (BIOS) or Uniform Extensible Firmware Interface (UEFI), and platform firmware 140. These software and/or firmware modules have varying functionality when their corresponding program code is executed by processor subsystem 132 or secondary processing devices within communication device 100. Data, such as carbon dioxide baseline threshold(s) 141 associated with contextual information 142 within location map 143, is stored in system memory 135.

Data storage subsystem 107 provides nonvolatile storage accessible to controller 106. For example, data storage subsystem 107 can provide a large selection of other applications 137 that can be loaded into system memory 135. Local data storage device(s) 144 can include hard disk drives (HDDs), optical disk drives, solid state drives (SSDs), etc. In one or more embodiments, removable storage device (RSD) 145 that is received in RSD interface 146 is a computer readable storage device, which can be referred to as non-transitory. RSD 145 is an example of a computer program product that can be accessed by controller 106 to provision communication device 100 with program code that when executed by controller 106 provides the functionality to communication device 100 to perform aspects of the present innovation described herein.

I/O subsystem 108 provides input and output devices, such as for detecting a person proximate to communication device 100. The input and output devices can also present content to or receive content from a user that is carried by OTA communication. For example, image capturing device 148, such as a camera, can receive gestures and other image data. User interface device 149 can present visual or tactile outputs as well as receive user inputs. Tactile/haptic control 150 can provide an interface such as for braille reading or manual inputs. Microphone 151 receives user audible inputs. Audio speaker 152 can provide audio output, including audio playback and alerts. Range finder 153 can emit a waveform of energy, such as acoustic, infrared, radio frequency (RF), etc., whose time of flight is used to measure distance to a reflecting object. I/O subsystem 108 can be wholly or substantially encompassed by device housing 154 or be connected via I/O controller 155 as a peripheral device such as a remote $CO_2$ sensor 102e. I/O controller 155 can also interface with wired local access network (LAN).

In one or more embodiments, communication device 100 can receive modular ("mod") device, such as biosensor mod device 156 that augments capabilities and functionalities of communication device 100. Other examples of mod devices include a stereo loud speaker, a display projector, a mobile printer, a voice commanded smart speaker, a gamepad, a style shell, a 360° camera, a power pack, a camera with optical zoom, a wireless charging shell, a custom developed mod, a fifth generation (5G) cellular data communication modem, etc. In one embodiment, housing 154 of communication device 100 includes a mounting surface that is shaped to conform to and engage with mod housing 157 of biosensor mod device 156. Magnets embedded in mod device 156 are attracted to ferrous material of device housing 154 to create engagement between communication device 100 and biosensor mod device 156. Biosensor mod device 156 can include an attachable $CO_2$ sensor 102f and other air sensors 158 such as for temperature, alcohol, and humidity. It is often inconvenient for users to check biological parameters related to their health. For example, a person's breath may be analyzed to make medical findings and inferences regarding the person's health. Gas sensors may be embedded with the device speech microphone assembly for measuring user and environmental volatile organic compounds (VOCs). Gas sensors may be in the form of an add-on device such as a MOTOROLA MOD, such as biosensor mod device 156, which is usable with one or more types of cellular devices.

Communication device 100 includes target sensing for determining whether one or more targets, such as person 126, is present in enclosed space 124. Target sensing can be based on electromagnetic, optical, acoustic, thermal, etc., radiated energy 159 that originates at, is caused by, or is reflected by person 126. Examples of target sensing at a distance includes use of image capturing device 148, microphone 151, and range finder 153. Target sensing can also be based on physical contact of person 126 detected by user interface device 149, motion sensing device 160, or antenna arrays 114a, 114b. As used herein, target refers to an object whose physical presence or action is directly or indirectly detected and that has some correlation with a human person. Correlating results from two different types of sensors reduces both false positive determinations and false negative determinations. A target sensor can help distinguish between human and non-human emitters, augmenting the accuracy of carbon dioxide sensor. A carbon dioxide sensor can detect a carbon dioxide emitter such as a person who is quiet or positioned out of the field of view of an image detector. For certain applications, settings can be based on positive indications from only one type of sensor in order to avoid a false negative. For example, communication device 100 can assure that an always on voice control is listening when there is a chance that a user is nearby. For certain applications, settings can be based on requiring agreement between both types of sensors for determining that a person is present. For certain applications, settings can be based on requiring agreement between both types of sensors for determining that a person is absent.

Target sensor(s) can be integrally attached to, detachably engaged to, or wirelessly networked to communication device 100. Examples of target sensing include one or more of: (i) image recognition by image capturing device 148 of communication device 100; (ii) range finding by time of flight of a range finding transmission by range finder 153 the communication device; (iii) human speech detection by at least one microphone of communication device 100; (iv) evaluation of back scatter return of a radio frequency (RF) transmit signal from transmitter(s) 113 of communication device 100; (v) touch detection detected by tactile control 150 of communication device 100; (vi) antenna blocking detection based on detuning of at least one antenna array 114a, 114b; and (vii) movement detection by movement sensor or motion sensing device 160 of communication device 100.

Sensing by communication device 100 can provide contextual information to conditions in which carbon dioxide and target sensing occur. Location of communication device 100 can be based on one or more of: (i) global positioning system (GPS) measurements; (ii) triangulation from fixed wireless nodes; (iii) dead reckoning based on a movement sensor or motion sensing device 160 from a geospatially determined location. Context can be associated with date, time, day of the week, day of the year, etc. Context can be associated by whether or not at least one target, presumed to be a person, is breathing close to a carbon dioxide sensor, and thus skews the results. For example, a communication device 100 can sense that a user is speaking into the communication device 100, causing a spike in the measured carbon dioxide level. The higher level would otherwise be associated with more than one person in the space. Conversely, as a lagging indicator when a person is distant from carbon dioxide sensing. Physical indications of a person entering or leaving enclosed space 124 can be detected immediately, such as recognizing sounds of walking and a door opening and closing. Operation of communication device 100 can be initially based on this audio-based target sensing until confirmation becomes available from carbon dioxide sensing. In other situations, such as when communication device 100 detects being carried into enclosed room 124, carbon dioxide levels in the room can be detected first before physical target sensing can confirm whether another person is present. A person already in the room elevates the carbon dioxide level in advance of the entry but may be quiet and out of view initially from communication device 100. Operation of communication device 100 can initially be based on carbon dioxide sensing.

In one or more embodiments, communication device 100 performs data fusion of carbon dioxide, target, and contextual information for creating or updating carbon dioxide baseline threshold. For example, range finder 153 and image capturing device 148 can enable estimates by person detection system application 136 to be made as to an air volume of enclosed space 124. Acoustic data from microphone 151 can enable determination of whether heating, air condition, and ventilation (HVAC) systems are active, reducing the opportunity to detect carbon dioxide emitters in enclosed space 124.

Figure 2:
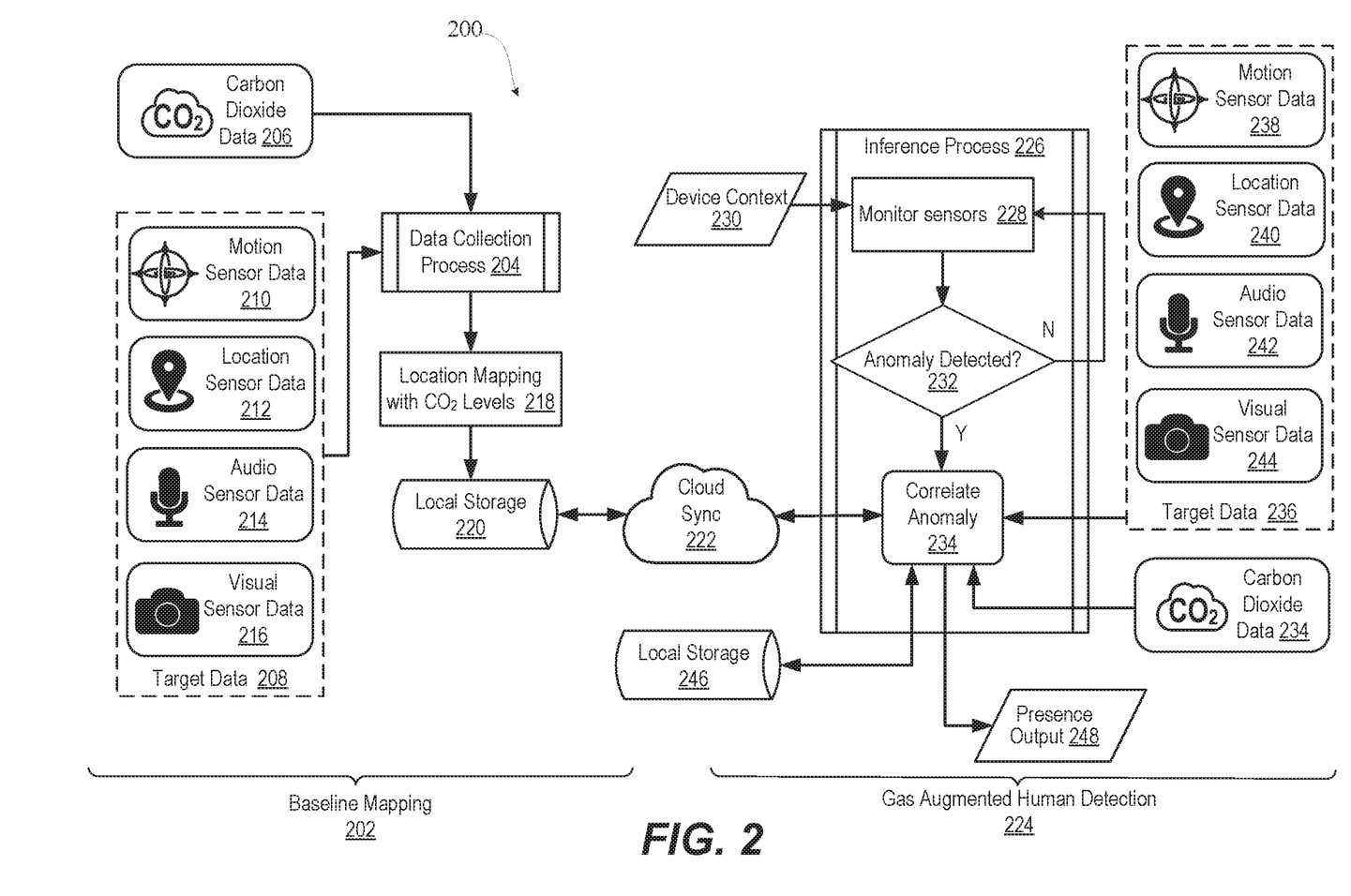
FIG. 2 is a system flow diagram of a gas augmented human detection system, according to one or more embodiments.

FIG. 2 illustrates gas augmented human detection system 200 that includes one or more communication devices 100 and $CO_2$ sensors 102 (FIG. 1). Gas augmented human detection system 200 contextually maps and uses $CO_2$ sensor data for increasing confidence in person detection. In one distributed or centralized process, baseline mapping procedure 202 is performed for contextually mapping $CO_2$ sensor data. Data collection process 204 receives carbon dioxide data 206 and target data 208 comprising one or more of motion sensor data 210, location sensor data 212, audio sensor data 214, and visual sensor data 216. Gas measurements of surrounding areas and variations in particular locations are collected and averaged over time. Correlating noise level, device inertial measurement unit (IMU) data, camera data, etc., can provide inferential information regarding human presence that provides context to the $CO_2$ sensor measurements. Detection of human presence can be based on directional information available from various sensors. For example, determination of presence of a human person can be based on an inference provided by a visual indication that coincides with an audio indication.

Carbon dioxide data 206 and target data 208 can be obtained from repurposed environmental sensors or controls using an Internet-of-Things (IoT) architecture or other networking arrangement. For example, fire detectors in each room of a house may obtain carbon dioxide readings continuously or intermittently. An Internet-coupled smart speaker can monitor sounds in a room. A security camera system can detect images within a room. A smart light switch can detect motion within a room. Fixed sensors can have an associated fixed location. Movable sensors can have an attached location sensing capability for associating location with other contextual information.

In one or more embodiments, data collection process 204 determines location mapping with $CO_2$ levels 218 by determining a carbon dioxide baseline threshold that is greater than a majority of the mapped carbon dioxide measurements for a corresponding location. When such a location is generally empty of persons, a majority of the measurements will be taken without any persons in the room. A baseline can be based on the majority of measurements. During rare instances, detecting that a current carbon dioxide level exceeds the carbon dioxide baseline threshold, the exceedance thus comprises an anomaly that indicates presence of a person. The amount of the exceedance can correspond to a number of persons that are present. This type of baselining can be used, for example, using an installed gas sensor in a facility that is not collocated with a target sensor. During overnight hours no communication devices with target sensing are present to confirm the absence of persons. However, the long duration of relatively low carbon dioxide levels along with context as to time of day can be used to determine a baseline that is associated with no carbon dioxide emitters.

In one or more embodiments, data collection process 204 has the benefit of gas emission augmented target sensing to associate carbon dioxide measurements with the presence or absence of persons. Data collection process 204 determines location mapping with $CO_2$ levels 218 by separating measurements when at least one person is detected from measurements in which no persons are detected. Thus, data collection process 204 determines a first subset of the mapped carbon dioxide measurements for a corresponding location that are associated with corresponding contextual information that does not confirm the presence of one or more targets in the space. Data collection process 204 determines a second subset of the mapped carbon dioxide measurements for the corresponding location associated with corresponding contextual information that confirms the presence of one or more targets in the enclosed space. Data collection process 204 defines the carbon dioxide baseline threshold that generally separates the first and second subsets.

In one or more embodiments, data collection process 204 determines location mapping with $CO_2$ levels 218 by determining the carbon dioxide baseline threshold that is greater than a majority of the mapped carbon dioxide measurements for one or more outside locations adjacent to the space. For example, buildings and facilities in a geographic area can generally have the same carbon dioxide reading as the outside environment unless persons are present in the respective buildings and facilities. Data collection process 204 can extrapolate baseline thresholds based on data taken in an adjacent room or building.

Data collection process 204 can store location mapping with $CO_2$ levels 218 either temporary or permanently on local storage 220. In one or more embodiments, data collection process 204 stores location mapping with $CO_2$ levels 218 on cloud sync storage 222 for wide scale integration and use by a population of communication devices that perform gas augmented human detection process 224. Each communication device performs inference process 226 that monitors sensors (block 228) with associated device context information 230. Based on device context 230, inference process 226 performs a determination of whether an anomaly is detected (decision block 232). If no anomaly is detected, then inference process 226 returns to monitoring sensors (block 228). If an anomaly is detected in either carbon dioxide data 234 or target data 236, then inference process 226 correlates the anomaly with the other one of carbon dioxide data 234 and target data 236 (block 234). Target data 236 comprises one or more of motion sensor data 238, location sensor data 240, audio sensor data 242, and visual sensor data 244. Based on the correlation, inference process 226 stores information in local storage 246 and updates cloud sync storage 222. Inference process 226 provides inferred human presence output 248 to other applications or components of communication device 100 (FIG. 1) to control features whose settings or operation depend on the absence or presence of one or more persons.

In one aspect, gas augmented human detection system 200 collects emission or air quality measurements in real time using additional available sensors and attempts to identify the most likely sources of the $CO_2$ emissions. This data is combined with other common contextual information, e.g., location and time, to provide a more complete and useful contextual map of emissions in an area.

In one aspect, gas augmented human detection system 200 augments current presence detection systems by using emissions, in particular $CO_2$ to increase confidence in, or provide an alternative to, vision, audio, or other sensors. Gas augmented human detection system 200 increases confidence in detection of the presence or absence of a person by correlating changes in different types of environmental and contextual information.

Figure 3:
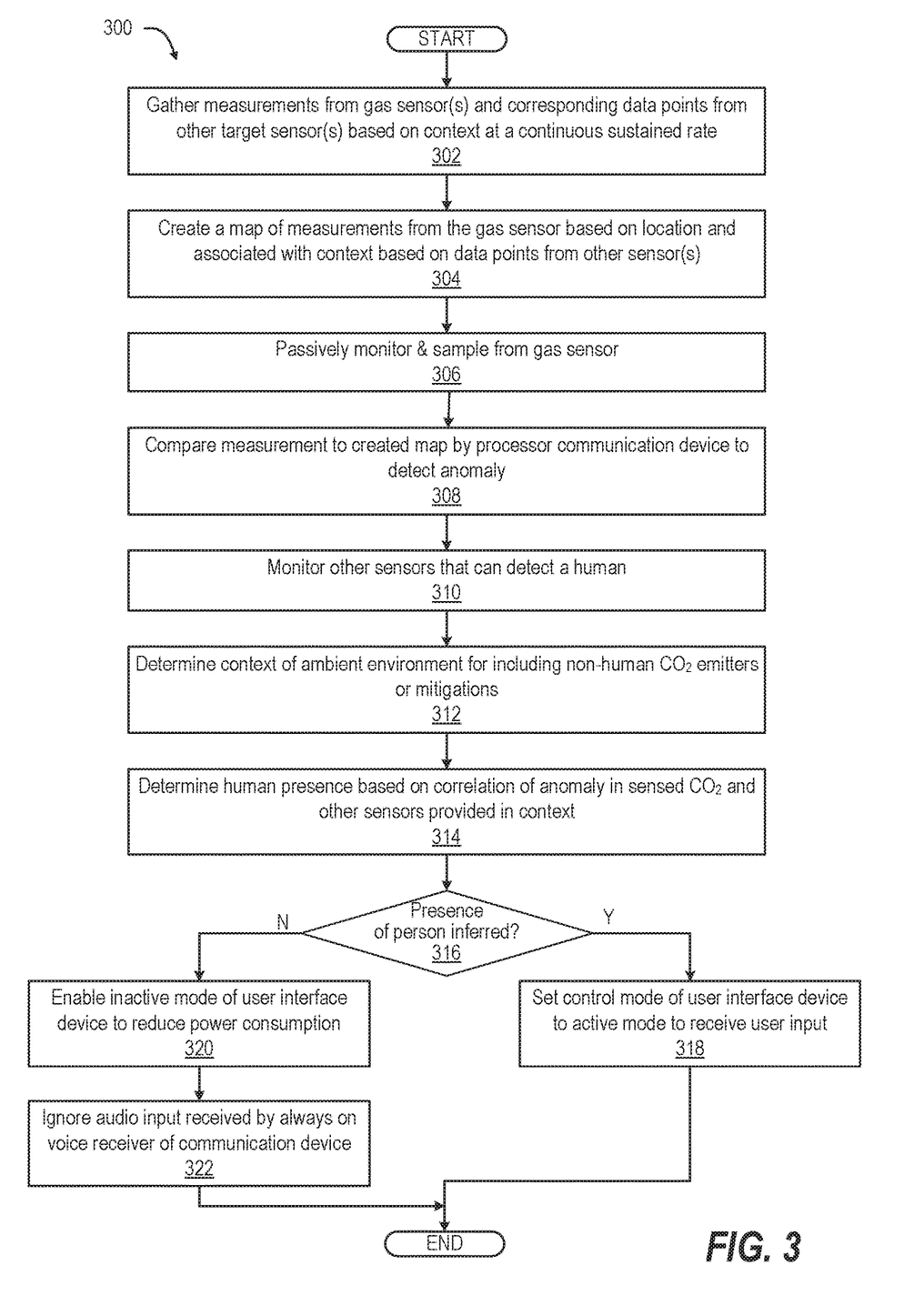
FIG. 3 is a flow diagram illustrating a method for mapping and utilizing contextual baseline emissions data for human presence detection, according to one or more embodiments.

FIG. 3 illustrates method 300 for mapping and utilizing contextual baseline emissions data for human presence detection. In one or more embodiments, method 300 includes gathering, by a centralized or distributed gas augmented human detection system 200 (FIG. 2), measurements from gas sensor(s) and corresponding data points from other target sensor(s) based on context at a continuous sustained rate (block 302). For example, context can include one or more of: (i) location; (ii) movement of the sensor; (iii) movement of a sensed target; (iv) date/time of measurement; (v) emission level; and (vi) number of targets sensed. Method 300 includes creating a map of measurements from the gas sensor based on location and associated with context based on data points from other sensor(s) (block 304). At a particular location, method 300 includes passively monitoring and sampling from gas sensor (block 306). Method 300 includes comparing measurement to created map by processor of communication device to detect anomaly (block 308). Method 300 includes monitoring other target sensors that can detect a human (block 310). Method 300 includes determining, by the processor, context of ambient environment for including non-human $CO_2$ emitters or mitigations (block 312). Method 300 includes determining, by the processor, human presence based on correlation of the anomaly in sensed $CO_2$ and other sensors provided in context (block 314). Method 300 includes communicating an inferred presence or absence of person(s) to an application or component of communication device whose operation responds to the presence or absence of a person.

In one or more embodiments, a determination is made whether the presence of a person is inferred (decision block 316). The inference can be based on the current carbon dioxide level being greater than the carbon dioxide baseline threshold. In response to determining that the presence of a person is inferred, method 300 includes setting the control mode of a user interface device of the communication device to an active mode to receive a user input (block 318). Then method 300 ends. In response to determining that the presence of a person is not inferred in decision block 316, method 300 includes enabling an inactive mode of the user interface device to reduce power consumption (block 320). In a particular embodiment, method 300 includes ignoring an audio input received by an always on voice receiver of the communication device to prevent an audio playback device in the space from being misinterpreted as a voice command from a person in the space (block 322). Then method 300 ends.

Carbon dioxide baseline threshold can be statically defined, especially during an early stage of deployment of the present innovation in which baseline data for a particular location is not available. In one or more embodiments, carbon dioxide baseline thresholds are dynamically determined for multiple locations and associated with a range of contextually associated situations. For example, certain times of year can affect the ambient carbon dioxide level in a locality as vegetation grows or withers. A nearby forest fire can have an effect on locations downwind for a period of time. Outside air temperatures can cause activation of heating, air condition, and ventilation systems that affect retention of carbon dioxide in enclosed spaces. Non-human carbon dioxide emitters, such as pets and fireplaces, may be more prevalently active indoors during winter months.

Figure 4:
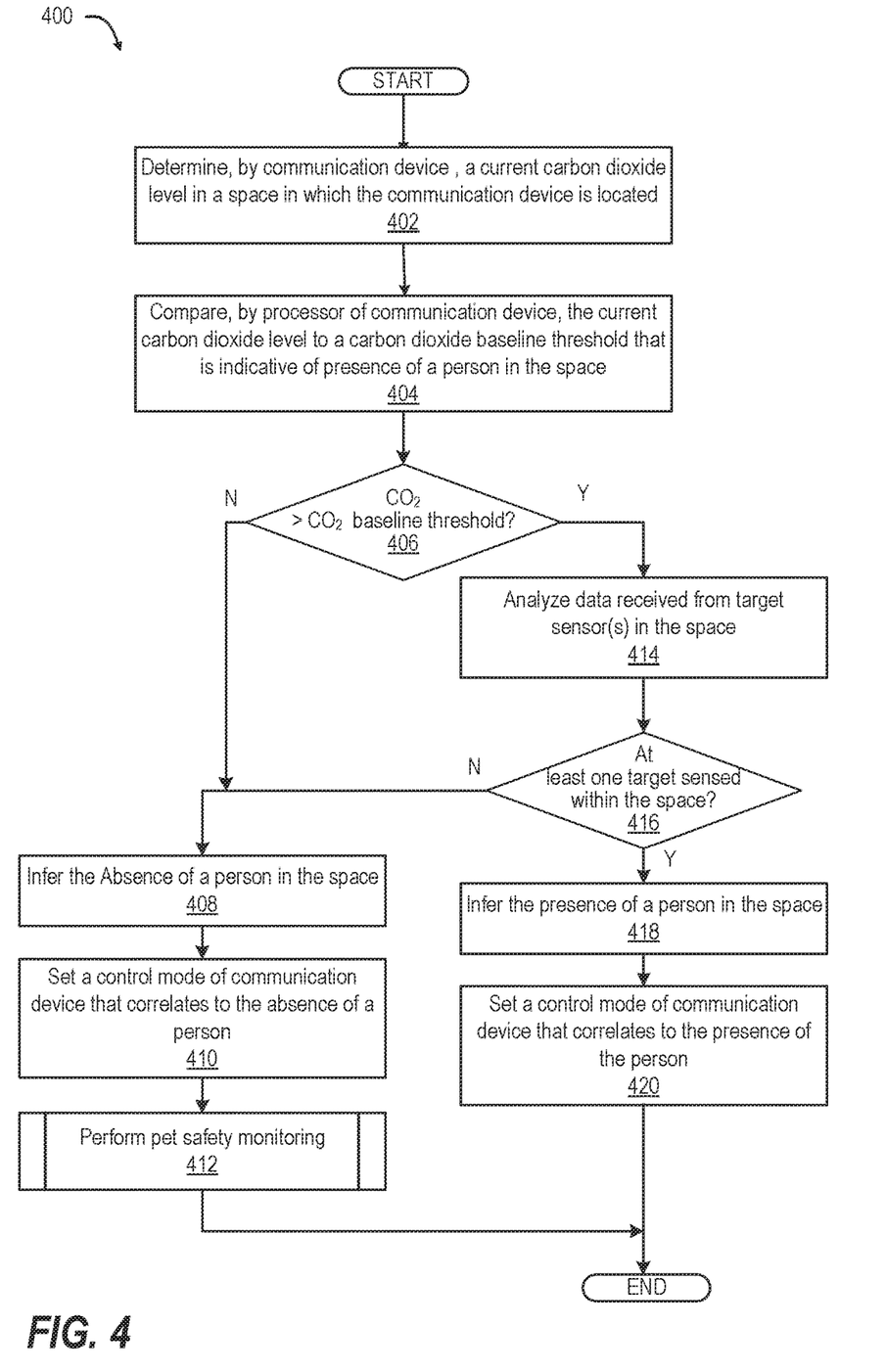
FIG. 4 is a flow diagram illustrating a method for inferring a presence of a person based on both sensing carbon dioxide emissions and a presence of a physical target, according to one or more embodiments.

FIG. 4 illustrates method 400 for inferring presence of a person based on both sensing carbon dioxide emissions and the presence of a physical target. In one or more embodiments, method 400 includes determining, by communication device 100 (FIG. 1), a current carbon dioxide level in a space in which the communication device is located (block 402). Method 400 includes comparing, by processor 132 of communication device 100 (FIG. 1), the current carbon dioxide level to a carbon dioxide baseline threshold that is indicative of presence of a person in the space (block 404). A determination is made whether the current carbon dioxide level is greater than the carbon dioxide baseline threshold (decision block 406). In response to determining that the current carbon dioxide level is not greater than the carbon dioxide baseline threshold, method 400 includes inferring the absence of a person in the space (block 408). Method 400 includes setting a control mode of communication device 100 (FIG. 1) that correlates to the absence of a person (block 410). Then method 400 ends. In response to determining that the current carbon dioxide level is greater than the carbon dioxide baseline threshold in decision block 406, method 400 includes analyzing data received from target sensor(s) in the space (block 412). A determination is made whether at least one target is sensed within the space (decision block 414). In response to determining that at least one target is not sensed in the space, method 400 proceeds to block 408. In response to determining that at least one target is sensed in the space in decision block 414, method 400 includes inferring the presence of a person in the space (block 416). Method 400 includes setting a control mode of communication device 100 (FIG. 1) that correlates to the presence of the person (block 418). Then method 400 ends.

Figure 5A:
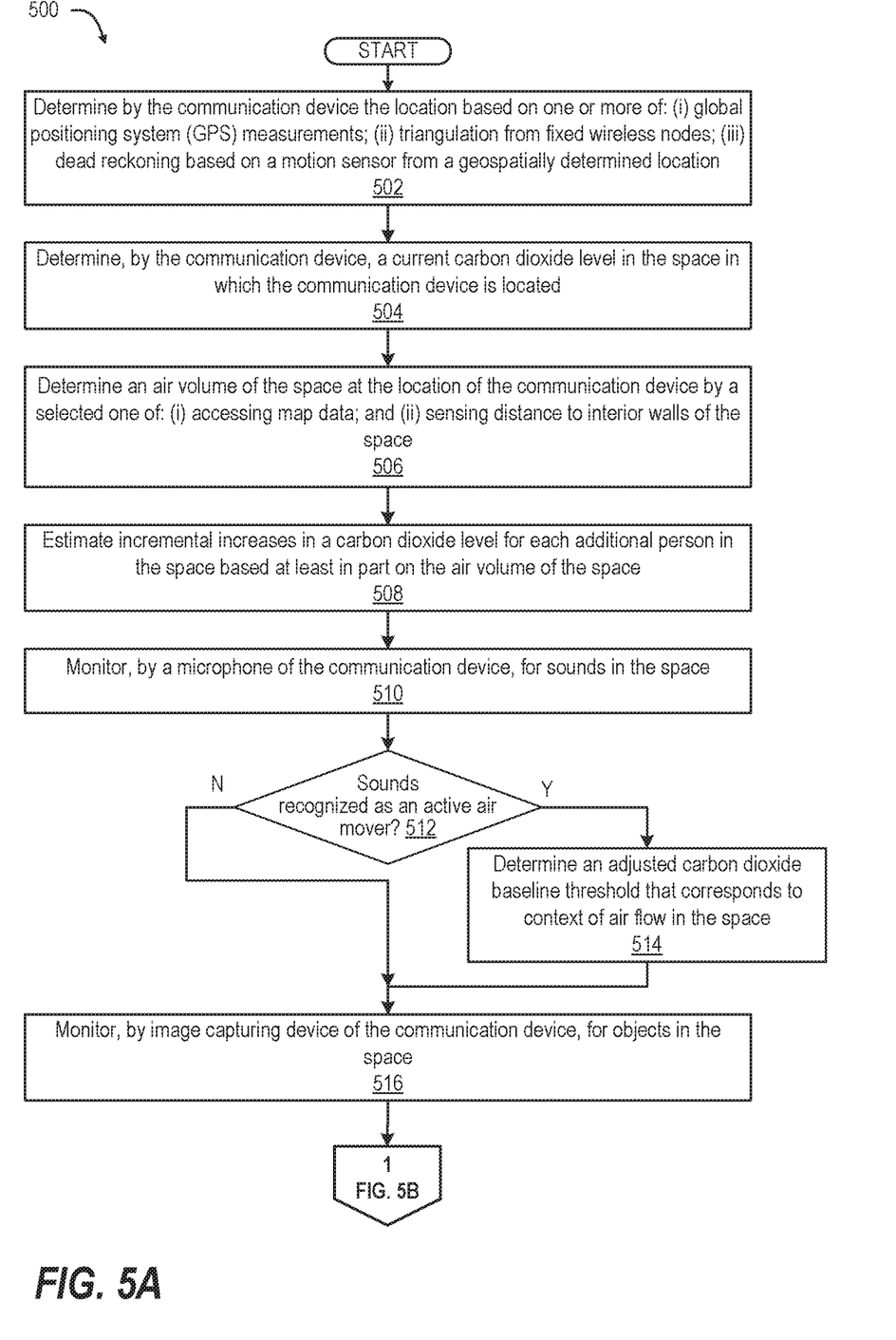
FIGS. 5A-5B are a flow diagram illustrating a method for determining human presence based on correlation of the anomaly in sensed $CO_2$ and other sensors provided in context, according to one or more embodiments.
Figure 5B:
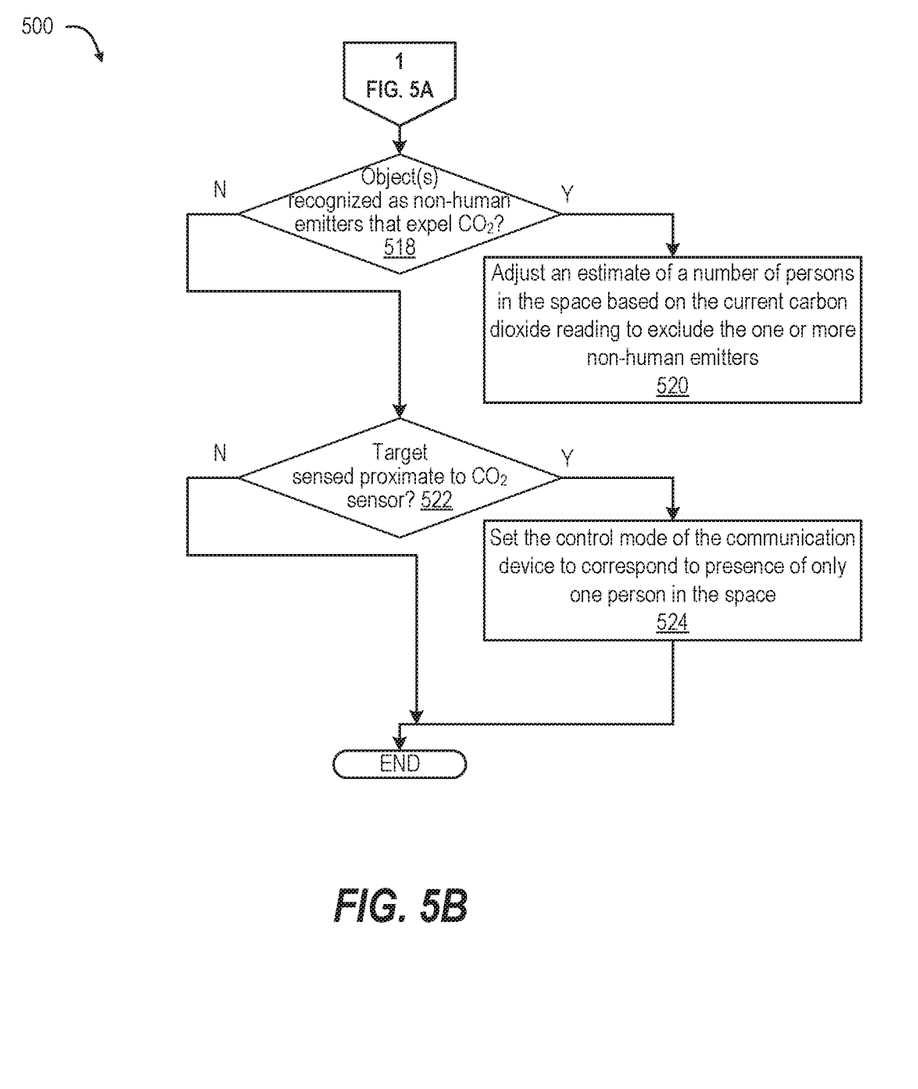

FIGS. 5A-5B illustrate method 500 for determining human presence based on correlation of the anomaly in sensed $CO_2$ and other sensors provided in context. In particular, method 500 adjusts for aggravating and mitigating factors that scale the contribution of carbon dioxide by each additional person to a space. In one or more embodiments, method 500 includes determining by the communication device the location based on one or more of: (i) global positioning system (GPS) measurements; (ii) triangulation from fixed wireless nodes; (iii) dead reckoning based on a motion sensor from a geospatially determined location (block 502). Method 500 includes determining, by communication device 100 (FIG. 1), a current carbon dioxide level in the space in which the communication device is located (block 504). Method 500 includes determining an air volume of the space at the location of the communication device by a selected one of: (i) accessing map data; and (ii) sensing distance to interior walls of the space (block 506). Method 500 includes estimating incremental increases in a carbon dioxide level for each additional person in the space based at least in part on the air volume of the space (block 508).

In one or more embodiments, method 500 includes monitoring, by a microphone of the communication device, for sounds in the space (block 510). A determination is made whether the sounds are recognized by controller 106 (FIG. 1) of the communication device as an active air mover (decision block 512). In response to determining that sounds are recognized as an air mover, method 500 includes determining an adjusted carbon dioxide baseline threshold that corresponds to context of air flow in the space (block 514).

In one or more embodiments, in response to determining that sounds are not recognized as an air mover in decision block 512 or after performing block 514, method 500 includes monitoring, by image capturing device 148 (FIG. 1) of the communication device, for objects in the space (block 516). Method 500 includes determining whether any objects in the space are recognized as non-human emitters that expel carbon dioxide (decision block 518). In response to determining that one or more objects in the space are recognized as non-human emitters that expel carbon dioxide, method 500 includes adjusting an estimate of a number of persons in the space based on the current carbon dioxide reading to exclude the one or more non-human emitters (block 520).

In one or more embodiments, in response to determining that one or more objects in the space are not recognized as non-human emitters that expel carbon dioxide or after performing block 520, method 500 includes determining whether one target is sensed proximate to the carbon dioxide sensor (block 522). In response to determining that one target is sensed proximate to the carbon dioxide sensor, method 500 includes setting the control mode of the communication device to correspond to presence of only one person in the space (block 524). In response to determining that one target is not sensed proximate to the carbon dioxide sensor in decision block 522 or after block 524, then method 500 ends.

In one or more embodiments, method 500 further comprises monitoring, by a microphone of the communication device, for sounds in the space. Method 500 includes determining, by a controller of the communication device, whether a specific sequence of sounds are identified, the specific sequence including a sound of a person moving within the enclosed space followed by a sound of a door opening and closing. In response to determining that the specific sequence of sounds is identified, method 500 includes (i) estimating an updated number of persons in the space that decrements a previously estimated number of persons; and (ii) monitoring for a decrease in the current carbon dioxide level to corroborate the updated estimate of persons.

In one or more embodiments, in determining whether the at least one target is sensed comprises, method 500 includes monitoring, by a microphone of the communication device, for sounds in the enclosed space. Method 500 includes determining, by a controller of the communication device, whether a specific sequence of sounds are identified, the specific sequence including a sound of a door opening and closing followed by a sound of a person moving within the space. In response to determining that the specific sequence sounds are identified, method 500 includes: (i) estimating an updated number of persons in the room that increments a previously estimated number of persons; and (ii) monitoring for an increase in the current carbon dioxide level to corroborate the updated estimate of persons.

Figure 6:
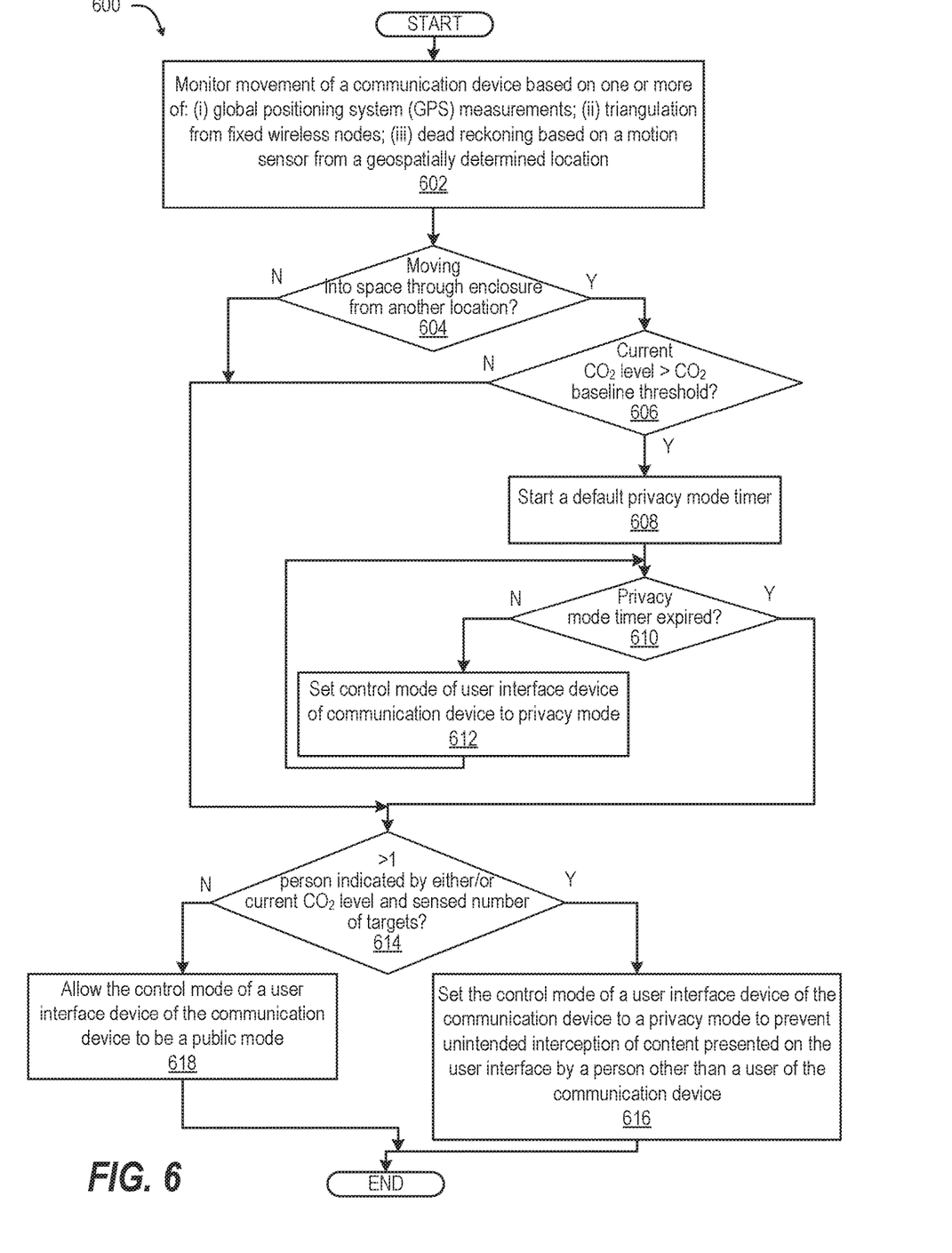
FIG. 6 is a flow diagram illustrating a method for setting user interface privacy based on gas augmented human presence detection, according to one or more embodiments.

FIG. 6 illustrates method 600 for setting user interface privacy based on gas augmented human presence detection. In one or more embodiments, method 600 comprises monitoring movement of a communication device based on one or more of: (i) global positioning system (GPS) measurements; (ii) triangulation from fixed wireless nodes; (iii) dead reckoning based on a motion sensor from a geospatially determined location (block 602). Method 400 includes determining, by the communication device, whether the communication device is moving into a space through an enclosure from another location (decision block 604). In response to determining that the communication device has moved inside of an enclosed space, a determination is made whether the current carbon dioxide level is greater than the carbon dioxide baseline threshold, indicating that a person is present in the enclosed space (decision block 606). In response to determining that the current carbon dioxide level is greater than the carbon dioxide baseline threshold, method 500 includes starting a default privacy mode timer (block 608). A determination is made whether the privacy mode timer has expired (decision block 610). In response to determining that the privacy mode timer has not expired, method 600 includes setting the control mode of a user interface device of the communication device to a privacy mode (block 612). The privacy mode prevents unintended interception of content presented on the user interface device by a person other than a user of the communication device until a target sensor can corroborate presence of the person. Then method 600 returns to decision block 610.

In response to any of: (i) determining that the privacy mode timer has expired in decision block 610; (ii) determining that the current carbon dioxide level is not greater than the carbon dioxide baseline threshold in decision block 606; or (iii) determining that the communication device has not moved inside of an enclosed space from another location in decision block 604, method 600 includes determining whether at least one of: (i) the current carbon dioxide level; and (ii) a sensed number of targets in the enclosed space indicates more than one person is present in the space (decision block 614). Method 600 includes, in response to determining that more than one person is present, setting the control mode of a user interface device of the communication device to a privacy mode to prevent unintended interception of content presented on the user interface by a person other than a user of the communication device (block 616). Then method 600 returns to block 602. In response to determining that more than one person is not present in decision block 614, method 600 includes allowing the control mode of a user interface device of the communication device to be a public mode (block 618). Then method 600 returns to block 602.

In one or more embodiments, method 600 includes determining whether the space is a selected type of vehicle based on one or more of: (i) a current location that is outside of a geographically defined enclosure; (ii) a wireless connection that self-identifies as associated with a vehicle; (iii) a detected spatial volume of the enclosed space that corresponds to a vehicle; and (iv) detecting aligned movement of the communication device and the enclosed space. The method 600 includes, in response to determining that the enclosed space is the selected type of vehicle: (i) associating the selected type of vehicle and the determined number of persons present with a default setting for one of; (i) privacy mode; and (ii) public mode. Method 600 includes overriding a privacy mode of the user interface to enable hands free operation in response to the default setting being public mode.

Figure 7:
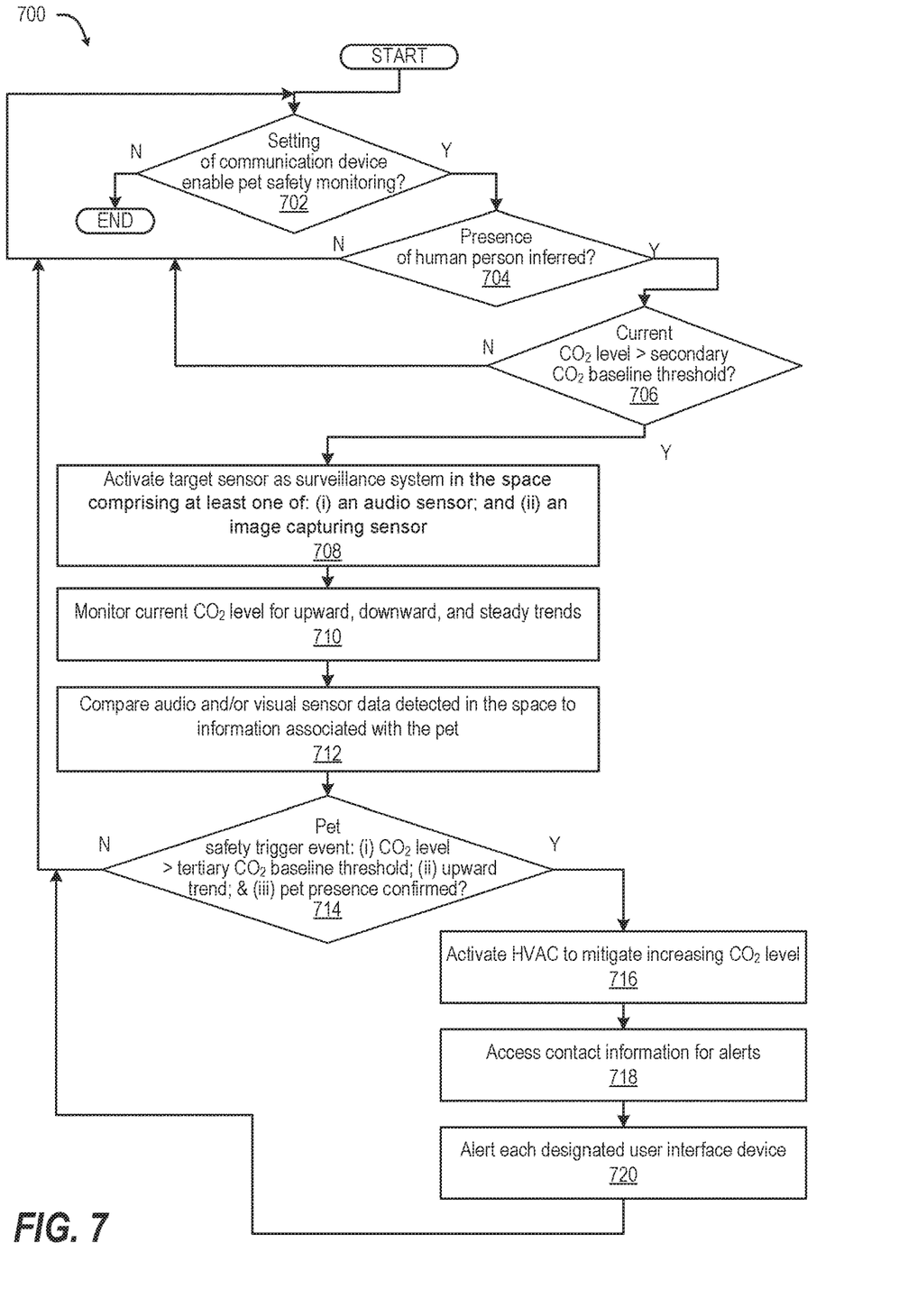
FIG. 7 is a flow diagram illustrating a method for monitoring pet safety based at least in part on carbon dioxide sensing.

FIG. 7 illustrates method 700 of monitoring pet safety based at least in part on carbon dioxide sensing. Method 700 includes determining whether a setting of communication device 100 (FIG. 2) enables pet safety monitoring (block 702). For example, the setting can be user selected based on whether a person owns a pet or not. In response to determining that a setting of the communication device 100 does not enable pet safety monitoring, method 700 ends. In response to determining that a setting of the communication device 100 enables pet safety monitoring, method 700 includes determining whether presence of a human person in a space is inferred (decision block 704). This determination can be made as described for method 400 (FIG. 4). In response to determining that the presence of a human person the space is inferred, method 700 returns to block 702. In response to determining that the presence of a human person the space is not inferred, method 700 includes determining whether a current carbon dioxide level is greater than a secondary carbon dioxide baseline threshold (decision block 706). In response to determining that the current carbon dioxide is not greater than a secondary carbon dioxide baseline threshold, method 700 returns to block 702. In response to determining that the current carbon dioxide is greater than a secondary carbon dioxide baseline threshold, method 700 includes activating a target sensor as a surveillance system in the space comprising at least one of: (i) an audio sensor; and (ii) an image capturing sensor (block 708). The surveillance system can be target sensors integral to communication device 100 (FIG. 1). The surveillance system can be security system installed in the space. The surveillance system can be sensors that repurposed for or dedicated to monitoring for presence of a pet in the space.

Method 700 includes monitoring, by communication device 100 (FIG. 1), carbon dioxide levels for upward, downward, and steady trends (block 710). Method 700 includes comparing audio and/or visual sensor data detected in the space to information associated with the pet (block 712). For example, presence of the pet can be based on determining whether the target is a pet based on at least one of: (i) a detected size of the target; (ii) a recognized sound from the target; or (iii) a detected rate of carbon dioxide emission by the target. Method 700 comprises determining whether all criteria for a pet safety trigger event are detected. In one or more embodiments, method 700 includes determining whether: (i) current carbon dioxide level is above a tertiary carbon dioxide level that is greater than the secondary carbon dioxide level; (ii) carbon dioxide level is trending upward; and (iii) presence of a pet is inferred based on both carbon dioxide level and target sensor confirmation (decision block 714). In response to determining that all of the criteria for a pet safety trigger event are not detected, method 700 returns to block 702. In response to determining that all of the criteria for a pet safety trigger event are detected, method 700 includes activating a heating, ventilation and air conditioning (HVAC) to mitigate increasing carbon dioxide level (block 716). For example, the space can be a vehicle having autostart and climate controls. For another example, the space can be house or facility having a ventilation fan or other air handling system. Method 700 includes accessing contact information in settings of communication device that are to be alerted when a pet safety trigger event is detected (block 718). Method 700 includes transmitting an alert to each designated user interface device (block 720). Then method 700 returns to block 702.

In one or more embodiments, audio or visual confirmation of presence of pet can be used to report confidence in detection of a pet that is initially based on carbon dioxide level. Safety measures for high carbon dioxide levels may be enabled even if audio or visual confirmation is not achieve, such as if the pet is sleeping out of sight of visual sensors. In one or more embodiments, confirmation of presence of the pet via an audio or visual target sensor can be a prerequisite prior to enabling safety mitigations. In one or more embodiments, certain pet safety mitigations can be enabled for carbon dioxide only based detection, such as generating user alerts. Certain pet safety measures that attempt to mitigate the carbon dioxide levels directly can require audio/visual confirmation of presence of the pet in the space.

In each of the above flow charts presented herein, certain steps of the methods can be combined, performed simultaneously or in a different order, or perhaps omitted, without deviating from the spirit and scope of the described innovation. While the method steps are described and illustrated in a particular sequence, use of a specific sequence of steps is not meant to imply any limitations on the innovation. Changes may be made with regards to the sequence of steps without departing from the spirit or scope of the present innovation. Use of a particular sequence is therefore, not to be taken in a limiting sense, and the scope of the present innovation is defined only by the appended claims.

As will be appreciated by one skilled in the art, embodiments of the present innovation may be embodied as a system, device, and/or method. Accordingly, embodiments of the present innovation may take the form of an entirely hardware embodiment or an embodiment combining software and hardware embodiments that may all generally be referred to herein as a "circuit," "module" or "system."

Aspects of the present innovation are described below with reference to flowchart illustrations and/or block diagrams of methods, apparatus (systems) and computer program products according to embodiments of the innovation. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

While the innovation has been described with reference to exemplary embodiments, it will be understood by those skilled in the art that various changes may be made, and equivalents may be substituted for elements thereof without departing from the scope of the innovation. In addition, many modifications may be made to adapt a particular system, device or component thereof to the teachings of the innovation without departing from the essential scope thereof. Therefore, it is intended that the innovation not be limited to the particular embodiments disclosed for carrying out this innovation, but that the innovation will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the innovation. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present innovation has been presented for purposes of illustration and description but is not intended to be exhaustive or limited to the innovation in the form disclosed. Many modifications and variations will be apparent to those of ordinary skill in the art without departing from the scope and spirit of the innovation. The embodiment was chosen and described in order to best explain the principles of the innovation and the practical application, and to enable others of ordinary skill in the art to understand the innovation for various embodiments with various modifications as are suited to the particular use contemplated.

What is claimed is:

1. A method comprising:
    determining, by a communication device, a current carbon dioxide level in a space in which the communication device is located;
    comparing, by a processor of the communication device, the current carbon dioxide level to a carbon dioxide baseline threshold that is indicative of presence of a person in the space; and
    in response to determining that the current carbon dioxide level is greater than the carbon dioxide baseline threshold:
        determining whether at least one target is sensed within the space;
        in response to determining that at least one target is sensed in the space, inferring the presence of a person in the space based on the current carbon dioxide level and at least one other contextual information;
        determining whether (i) the current carbon dioxide level and (ii) a sensed number of targets in the space indicates more than one person is present in the space;
        in response to determining that more than one person is present in the space, setting a control mode of the communication device to a privacy mode that correlates to the presence of the more than one person in the space; and
        in response to determining that only one person is present in the space, setting a control mode of the communication device to a public mode.

2. The method of claim 1, further comprising:
    determining a geographic location of the space based one or more of: (i) global positioning system (GPS) measurements; (ii) triangulation from fixed wireless nodes; (iii) dead reckoning based on a motion sensor from a geospatially determined location;
    determining a spatial volume of the space at the geographic location; and
    determining an estimate of carbon dioxide contributions of each human emitter in the space based at least in part on an air volume.

3. The method of claim 1, wherein:
    determining a current carbon dioxide level comprises measuring the current carbon dioxide level in the space by a carbon dioxide sensor that is a selected one of: (i) integrally attached to; (ii) detachably engaged to; and (iii) wirelessly networked to the communication device; and
    determining whether at least one target is sensed comprises sensing the at least one target by a target sensor that is a selected one of: (i) integrally attached to; (ii) detachably engaged to; and (iii) wirelessly networked to the communication device.

4. The method of claim 1, wherein sensing whether at least one target is within the space comprises performing, via the target sensor, one or more of: (i) image recognition by an image capturing device of the communication device; (ii) range finding by time of flight of a range finding transmission by the communication device; (iii) human speech detection by at least one microphone of the communication device; (iv) evaluation of back scatter return of a radio frequency (RF) transmit signal from a transmitter of the communication device; (v) touch detection detected by a touch sensor of the communication device; (vi) antenna blocking detection based on detuning of at least one antenna; and (vii) movement detection by a movement sensor of the communication device.

5. The method of claim 1, wherein:
  determining a current carbon dioxide level comprises receiving carbon dioxide measurements from one or more carbon dioxide sensors at more than one location; and
  the method further comprises:
    receiving contextual information from one or more target sensors that detect targets proximate to the one or more target sensors;
    determining respective locations of the one or more carbon dioxide sensors and the one or more target sensors;
    mapping the received carbon dioxide measurements associated with corresponding contextual information based on respective locations; and
    determining the carbon dioxide baseline threshold for respective spaces based on the mapped carbon dioxide measurements.

6. The method of claim 5, further comprising
  determining the carbon dioxide baseline threshold that is greater than a majority of the mapped carbon dioxide measurements for a corresponding location that such a current carbon dioxide level exceeding the carbon dioxide baseline threshold comprises an anomaly.

7. The method of claim 5, further comprising:
  determining a first subset of the mapped carbon dioxide measurements for a corresponding location that are associated with corresponding contextual information that does not confirm the presence of one or more targets in the space;
  determining a second subset of the mapped carbon dioxide measurements for the corresponding location associated with corresponding contextual information that confirms the presence of one or more targets in the space; and
  defining the carbon dioxide baseline threshold that separates the first and second subsets.

8. The method of claim 1, further comprising:
  setting the control mode of a user interface device of the communication device to an active mode to receive a user input in response to determining that the current carbon dioxide level is greater than the carbon dioxide baseline threshold; and
  enabling an inactive mode of the user interface device to reduce power consumption in response to determining that the current carbon dioxide level is not greater than the carbon dioxide baseline threshold.

9. The method of claim 8, wherein enabling the inactive mode comprises ignoring an audio input received by an always on voice receiver of the communication device to prevent an audio playback device in the space from being misinterpreted as a voice command from a person in the space.

10. The method of claim 1, wherein the setting of the control mode comprises:
  and
  setting the control mode of a user interface device of the communication device to the privacy mode to prevent unintended interception of content presented on the user interface by a person other than a user of the communication device.

11. The method of claim 1, further comprising:
  determining whether the space is a selected type of vehicle based on one or more of: (i) a current location that is outside of a geographically defined enclosure; (ii) a wireless connection that self-identifies as associated with a vehicle; (iii) a detected spatial volume of the space that corresponds to a vehicle; and (iv) detecting aligned movement of the communication device and the space; and
  in response to determining that the space is the selected type of vehicle:
    associating the selected type of vehicle and the determined number of persons present with a default setting for one of: (i) privacy mode; and (ii) public mode; and
    overriding a privacy mode of the user interface to enable hands free operation in response to the default setting being public mode.

12. The method of claim 1, further comprising:
  in response to determining that the current carbon dioxide level indicates more than one person is present in the space, determining whether one target is sensed proximate to the carbon dioxide sensor;
  in response to determining that one target is sensed proximate to the carbon dioxide sensor, setting the control mode to correspond to the presence of only one person in the space; and
  in response to determining that no target is sensed proximate to the carbon dioxide sensor, setting the control mode to correspond to the presence of more than person in the space.

13. The method of claim 1, wherein:
  determining whether the communication device is within the space further comprises at least one of: (i) determining that a current location of the communication device is within a geographically defined enclosure; and (ii) detecting a spatial volume of the enclosure by the target sensor of the communication device; and
  the method further comprises estimating incremental increases in a carbon dioxide level for each additional person in the space based at least in part on an air volume of the space.

14. The method of claim 1, further comprising:
  determining that the communication device is moving;
  determining by the communication device that the communication device is moving into the space through an enclosure from another location based on one or more of: (i) global positioning system (GPS) measurements; (ii) triangulation from fixed wireless nodes; (iii) dead reckoning based on a motion sensor from a geospatially determined location; and
  in response to determining that: (i) the communication device has moved inside of the space; and (ii) the current carbon dioxide level is greater than the carbon dioxide baseline threshold, indicating that a person is present in the space:
    starting a default privacy mode timer; and
    setting the control mode of a user interface device of the communication device to a privacy mode until the default privacy mode timer expires to prevent unintended interception of content presented on the user interface device by a person other than a user of the communication device until a target sensor can corroborate presence of the person.

15. The method of claim 1, wherein determining whether the at least one target is sensed comprises:
  monitoring, by a microphone of the communication device, for sounds in the space;
  determining, by a controller of the communication device, whether a specific sequence of sounds are identified, the specific sequence including a sound of a person moving within the space followed by a sound of a door opening and closing;

in response to determining that the specific sequence of sounds is identified:
estimating an updated number of persons in the space that decrements a previously estimated number of persons; and
monitoring for a decrease in the current carbon dioxide level to corroborate the updated estimate of persons.

16. The method of claim 1, wherein determining whether the at least one target is sensed comprises:
monitoring, by a microphone of the communication device, for sounds in the space;
determining, by a controller of the communication device, whether a specific sequence of sounds are identified, the specific sequence including a sound of a door opening and closing followed by a sound of a person moving within the space; and
in response to determining that the specific sequence sounds are identified:
estimating an updated number of persons in the room that increments a previously estimated number of persons; and
monitoring for an increase in the current carbon dioxide level to corroborate the updated estimate of persons.

17. The method of claim 1, further comprising:
monitoring, by a microphone of the communication device, for sounds in the space;
determining whether the sounds are recognized by a controller of the communication device as an active air mover;
in response to determining that sounds are recognized as an air mover, determining an adjusted carbon dioxide baseline threshold that corresponds to context of air flow in the space;
monitoring, by an image capturing device of the communication device, for objects in the space;
determining whether any objects in the space are recognized as non-human emitters that expel carbon dioxide; and
in response to determining that one or more objects in the space are recognized as non-human emitters that expel carbon dioxide, adjusting an estimate of a number of persons in the space based on the current carbon dioxide reading to exclude the one or more non-human emitters.

18. The method of claim 1, wherein, in response to determining that at least one target is sensed in the space, the method comprises:
determining whether the target is a pet based on at least one of: (i) a detected size of the target; (ii) a recognized sound from the target; and (iii) a detected rate of carbon dioxide emission by the target; and
in response to determining that a pet is present in the space, setting a control mode of the communication device to a mode that correlates to the presence of a pet in the space, the mode comprising a selected at least one of: (i) activating a target sensor in the room; (ii) alerting a user interface device as to the current carbon dioxide level in the space; and (ii) activating a climate control system of the space.

19. A communication device comprising:
a carbon dioxide sensor;
a target sensor;
a memory containing a person detection system application and a carbon dioxide baseline threshold that is indicative of a presence of a person within a space;
a controller communicatively coupled to the carbon dioxide sensor, the target sensor, and the memory, and that executes the person detection system application, which causes the communication device to:
determine, via the carbon dioxide sensor, a current carbon dioxide level in the space;
compare the current carbon dioxide level to the carbon dioxide baseline threshold; and
in response to determining that the current carbon dioxide level is greater than the carbon dioxide baseline threshold;
determine whether at least one target is sensed within the space;
in response to determining that at least one target is sensed in the space, inferring the presence of a person in the space based on the current carbon dioxide level and at least one other contextual information;
determining whether (i) the current carbon dioxide level and (ii) a sensed number of targets in the space indicates more than one person is present in the space;
in response to determining that more than one person is present in the space, setting a control mode of the communication device to a privacy mode that correlates to the presence of the more than one person in the space; and
in response to determining that only one person is present in the space, setting a control mode of the communication device to a public mode.

20. A computer program product comprising:
a computer readable storage device; and
program code on the computer readable storage device that when executed by a processor associated with a communication device, the program code enables the communication device to provide the functionality of:
determining a current carbon dioxide level in a space;
comparing the current carbon dioxide level to a carbon dioxide baseline threshold that is indicative of presence of a person in the space; and
in response to determining that the current carbon dioxide level is greater than the carbon dioxide baseline threshold:
determining whether at least one target is sensed within the space;
in response to determining that at least one target is sensed in the space, inferring the presence of a person in the space based on the current carbon dioxide level and at least one other contextual information;
determining whether (i) the current carbon dioxide level and (ii) a sensed number of targets in the space indicates more than one person is present in the space;
in response to determining that more than one person is present in the space, setting a control mode of the communication device to a privacy mode that correlates to the presence of the more than one person in the space; and
in response to determining that only one person is present in the space, setting a control mode of the communication device to a public mode.

* * * * *